United States Patent [19]

Morita et al.

[11] Patent Number: 5,030,732
[45] Date of Patent: Jul. 9, 1991

[54] AMINOETHYLPHOSPHINIC ACID DERIVATIVES

[75] Inventors: Yoshiharu Morita, Yokohama; Yasuo Hoshide, Okegawa; Ryoichi Ando, Yokohama; Masao Taniguchi, Machida, all of Japan

[73] Assignee: Merck & Co., Inc., Rahway, N.J.

[21] Appl. No.: 163,440

[22] Filed: Mar. 3, 1988

[51] Int. Cl.$^5$ .................. C07F 9/32; C07F 9/572; C07F 9/6506
[52] U.S. Cl. .................. 548/344; 530/331; 548/496; 548/537; 560/38; 560/39; 560/40; 560/41; 560/153; 560/168; 560/169; 562/15; 562/16; 562/17
[58] Field of Search .................. 548/344, 496, 537; 560/38, 39, 40, 41, 153, 168, 169; 562/15, 16, 17; 530/331

[56] References Cited

U.S. PATENT DOCUMENTS

| | | | |
|---|---|---|---|
| 4,147,780 | 4/1979 | Dingwall | 424/211 |
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |
| 4,374,131 | 2/1983 | Petrillo | 424/200 |
| 4,416,833 | 11/1983 | Karanewsky et al. | 260/941 |
| 4,539,208 | 9/1985 | Kahen et al. | 514/195 |
| 4,715,994 | 12/1987 | Parsons et al. | 260/502.5 E |

FOREIGN PATENT DOCUMENTS

| | | |
|---|---|---|
| 0091594 | 10/1983 | European Pat. Off. . |
| 161546 | 11/1985 | European Pat. Off. . |
| 209848 | 1/1987 | European Pat. Off. . |
| 210545 | 2/1987 | European Pat. Off. . |

OTHER PUBLICATIONS

F. Arndt Organic Syn. Coll. V II 165-167, p. 33 (1943).
F. R. Atherton et al., Antimicrobial Agents & Chemoth. 15. 677 (1979).
P. A. Bartlett and W. B. Kezer, J. Amer. Chem. Soc. 106 4282-4283 (1979).
E. K. Baylis et al., J. Chem. Soc. Perkin Trans 1 2845-2853 (1984).
M. Bergmann & H. Schleich, Z. Physiol. Chem. Soc. 205, pp. 65-75 (1966).
B. J. Campbell et al., Biochem Biophys Acta 118, pp. 371-386 (1966).
Chem Abstracts, vol. 107, No. 11, No. 97134K (1987).
Chem Abstracts, vol. 107 (9), No. 78205d (1987).
Chaiet et al., J. Antibiotics 37 (3) 207-210 (1984).
Gundermann et al., Chem. Bes. 94 3254 (1961).
F. M. Kahan et al., J. Antimicrobial Chemo. 12, Suppl. D, 1-35 (1983).
Lesiak et al., Polish J. Chem. 53 327 (1979).
Neuhaus, J. Biol. Chem., 778 (1962).
F. C. Neuhaus & W. P. Hammes, Pharm. Ther. 14 265-319 (1981).
F. C. Neuhaus & J. L. Lynch, Biochemistry 3 471-480 (1964).
F. C. Neuhaus et al., Biochemistry 8 5119-5124 (1969).
A. Rahman et al., Tetrahedron 36 1063-1070 (1980).
E. D. Thorsett et al., (Merck & Co., Inc., Proc. Natl. Acad. Sci. U.S.A., vol. 79 2176-2180 (Apr. 1982).
J. K. Thottathil et al., Tetrahedron Lett. 25 4737-40, 4741-44 (1984).

*Primary Examiner*—Richard L. Raymond
*Attorney, Agent, or Firm*—Frank P. Grassler; Robert J. North; Hesna J. Pfeiffer

[57] ABSTRACT

Disclosed are some new aminoethylphosphinic acid derivatives useful as antibacterial agents.

6 Claims, No Drawings

AMINOETHYLPHOSPHINIC ACID DERIVATIVES

BACKGROUND OF THE INVENTION

This invention concerns some new aminoethylphosphinic acid derivatives. Specifically the invention concerns some new aminoethylphosphinic acid derivatives which have antibacterial action.

Among the many antibacterial agents reported to date, compounds which inhibit the biosynthesis of cell wall peptidoglycan (not found in higher animals) are noted for their safety and their selective toxicity. They include the β-lactams such as the penicillins, cephalosporins, single lactams and carbapenems, cycloserine, and bacitracin.

In the biosynthesis of cell wall peptidoglycan, the precursor which is UDP-MurNAc-Ala-D-Glu-Lys-D-Ala-D-Ala is first formed. Many enzymatic reactions are involved, including the conversion of L-Ala into D-Ala by the action of racemase, formation of D-Ala-D-Ala from D-Ala by the action of D-Ala-D-Ala ligase, and the binding of D-Ala D-Ala to UDP-MurNAc-Ala-D-Glu-Lys.

It is known that certain phosphonic acids have antibacterial action, as exemplified by alaphosphalin:

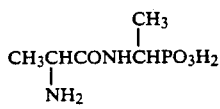

This compound is an inhibitor of bacterial cell wall synthesis. Its mechanism is reported to consist in the compound being taken up by the bacterium via the di-peptide transport system followed by scission of the peptide bond by the bacterium's peptidase, the 1-aminoethylphosphonic acid formed thereby inhibiting racemase activity.

(For examples, see Neuhaus, F.C. and Hammes, W.P.: Pharmacology & Therapeutics 14, 265–319, 1981; Atherton et al: Antimicrobial Agent and Chemotherapy 24, 552–528, 1983).

With this background, we sought a new and more effective antibacterial agent, and discovered the new type of aminoethylphosphonic acid derivatives to be described were effective agents. This discovery led to the present invention.

SUMMARY OF THE INVENTION

By this invention there is provided some aminoethylphosphinic acid derivatives represented by Formula I,

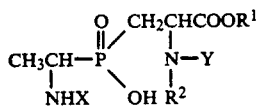

in which X may be hydrogen, acyl, or amino acid or oligopeptide residue with or without protection; Y may be hydrogen, alkylacyl with or without protection, or amino acid or oligopeptide residue with or without protection; and R$^1$ and R$^2$ may be hydrogen or alkyl.

(2) Derivatives in which the structure is represented by Formula III,

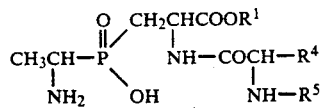

in which R$^1$ may be hydrogen or alkyl, R$^4$ may be alkyl or benzylthioalkyl, and R$^5$ may be amino acid or oligopeptide residue with or without protection.

(3) Derivatives, in which R$^1$ in Formula III is hydrogen, R$^4$ is n-propyl or benzylthiomethyl, and R$^5$ may be alanyl, phenylalanyl, leucyl, isoleucyl, norvalyl, sarcosyl, sarcosylalanyl or alanyl-alanyl.

(4) Derivatives in which the structure is represented by Formula IV,

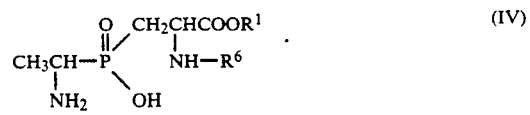

in which R$^1$ is hydrogen or alkyl and R$^6$ is amino acid residue with or without protection.

(5) Derivatives in which R$^1$ is hydrogen and R$^6$ may be lysyl, seryl, alanyl, norvalyl, o-benzylseryl, or S-benzylcysteine.

DETAILED DESCRIPTION OF THE INVENTION

In the following description of our invention, Formula I will represent the aminoethylphosphinic acid derivatives of our invention.

In Formula I, X may be hydrogen, alkylacyl such as acetyl and propionyl, arylacyl such as benzoyl, or amino acid or oligopeptide residue with or without the usual type of protection groups such as N-carbobenzyloxy, N-tert-butyloxycarbonyl, N-acetyl, O-benzyl, and S-benzyl.

By amino acid or oligopeptide residue is meant amino acid or oligopeptide in which the -OH from the carboxyl terminal has been removed. Examples of these amino acids are glycine, alanine, valine, leucine, isoleucine, serine, threonine, phenylalanine, tyrosine, tryptophan, histidine, aspartic acid, asparagine, glutamic acid, glutamine, lysine, arginine, crysteine, methionine, proline, norvaline, sarcosine, S-alkylcysteine or amino acid represented by Formula II,

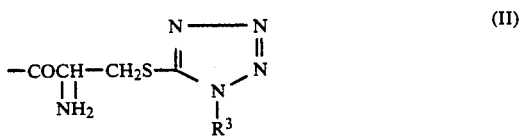

in which R$^3$ may be hydrogen, C$_{1-6}$ alkyl or cyclohexyl, or phenyl with or without substitution. Glycine, alanine, valine, leucine, isoleucine, serine, cysteine, methionine and norvaline are preferred.

The oligopeptide is a substance consisting of not more than 10, preferably not more than 5 of the above amino acids. Examples are alanyl-norvalyl, norvalyl-norvalyl, alanyl-alanyl-norvalyl, and methionyl-alanyl-norvalyl.

The amino acids and the oligopeptide components have optical isomers. The configuration may be D-, L- or DL-.

In Formula I, Y may be hydrogen, $C_{1-10}$alkylacyl such as acetyl, propionyl or phenylpropionyl with or without substitutents such as phenyl, napthyl or bi-phenyl, amino acid residue with or without protective groups named above, preferably glycine, alanine, valine, leucine, isoleucine, serine, phenylalanine, tyrosine, cysteine, methionine, norvaline or sarcosine, or oligopeptide residue with or without the protective groups named above, preferably alanyl-norvalyl, phenylalanyl-norvalyl, norvalyl-norvalyl, leucyl-norvalyl, isoleucyl-norvalyl, sarcosyl-norvalyl, alanyl-alanyl-norvalyl, sarcosyl-alanyl-norvalyl, alanyl-S-benzylcysteinyl or norvalyl-S-benzyl-cysteinyl.

Also in Formula I, $R^1$ and $R^2$ may be hydrogen or alkyl, i.e., $C_{1-6}$ straight or branched alkyl.

The aminoethylphosphinic acid derivatives of our invention are usually in the form of inner salts, but they may also be salts of other acids or bases. Examples are salts of mineral acids such as hydrochloric, hydrobromic and sulfuric acids, or salts of organic acids such as formic and acetic acids with the amine part; and salts of alkali or alkali earth metals such as sodium, potassium, calcium or magnesium, ammonium, or organic amines such as triethylamine and cyclohexylamine with the carboxylic and phosphinic acid parts.

In terms of antibacterial activity, compounds represented by Formula III or IV are preferred. These are represented by the following formulae,

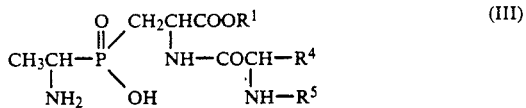
(III)

in which $R^1$ may be hydrogen or alkyl; $R^4$ may be alkyl or benzylthioalkyl; and $R^5$ in amino acid residue or oligopeptide residue such as sarcosylalanyl, alanyl-alanyl, and alanyl-norvalyl, with or without protection; preferably $R^1$ should be hydrogen, $R^4$ should be n-propyl or benzylthiomethyl, and $R^5$ should be alanyl, phenylalanyl, leucyl, isoleucyl, norvalyl or sarcosyl; and in Formula IV,

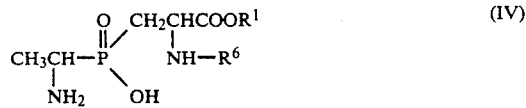
(IV)

$R^1$ may be hydrogen or alkyl and $R^6$ an amino acid residue which may or may not be protected. Preferably $R^1$ should be hydrogen and $R^6$ should be lysyl, seryl, alanyl, norvalyl, methionyl, O-benzylseryl, S-methylcysteinyl or S-benzylcysteinyl.

Specific examples of peptide derivatives of phosphinic acids of our invention are the following:
1. (1-Aminoethyl)(2-amino-2-carboxyethyl)phosphinic acid
2. (1-Aminoethyl)[2-(3-phenylpropionylamino)-2-carboxyethyl]phosphinic acid
3. (1-Aminoethyl)[2-(3-phenylpropionylamino)-2-(methoxycarbonyl)ethyl]phosphinic acid
4. (1-Aminoethyl)(2-L-phenylalanylamino-2-carboxyethyl)phosphinic acid
5. (1-Aminoethyl)(2-L-phenylalanylamino-2-methoxycarbonylethyl)phosphinic acid
6. (1-Aminoethyl)(2-L-norvalylamino-2-carboxyethyl)phosphinic acid
7. (1-Aminoethyl)(2-D-norvalylamino-2-carboxyethyl)phosphinic acid
8. (1-Aminoethyl)(2-L-leucylamino-2-carboxyethyl)phosphinic acid
9. (1-Aminoethyl)(2-L-isoleucylamino-2-carboxyethyl)phosphinic acid
10. (1-Aminoethyl)(2-L-methionylamino-2-carboxyethyl)phosphinic acid
11. (1-Aminoethyl)[2-S-(1-methyltetrazol-5-yl)crysteinylamino-2-carboxyethyl)phosphinic acid
12. (1-Aminoethyl)(2-L-alanylamino-2-carboxyethyl)phosphinic acid
13. (1-Aminoethyl)(2-L-Lysylamino-2-carboxyethyl)phosphinic acid
14. ((1-Aminoethyl)(2-L-serylamino-2-carboxyethyl)phosphinic acid
15. (1-Aminoethyl)(2-O-benzyl-L-serylamino-2-carboxyethyl)phosphinic acid
16. (1-Aminoethyl)(2-S-benzyl-L-cysteinylamino-2-carboxyethyl)phosphinic acid
17. (1-Aminoethyl)(2-S-methyl-L-cysteinylamino-2-carboxyethyl)phosphinic acid
18. (1-L-Norvalylaminoethyl)(2-L-phenylalanylamino-2-carboxyethyl)phosphinic acid
19. (1-Acetoaminoethyl)(2-L-norvalylamino-2-carboxyethyl)phosphinic acid
20. (1-Aminoethyl)(2-L-alanyl-L-norvalylamino-2-carboxyethyl)phosphinic acid
21. (1-Aminoethyl)(2-L-phenylalanyl-L-norvalylamino-2-carboxyethyl)phosphinic acid
22. (1-Aminoethyl)(2-L-norvalyl-L-norvalylamino2-carboxyethyl)phosphinic acid
23. (1-Aminoethyl)(2-L-leucyl-L-norvalylamino-2-carboxyethyl)phosphinic acid
24. (1-Aminoethyl)(2-L-isoleucyl-L-norvalylamino-2-carboxyethyl)phosphinic acid
25. (1-Aminoethyl)(2-sarcosyl-L-norvalylamino-2-carboxyethyl)phosphinic acid
26. (1-Aminoethyl)(2-L-alanyl-L-alanyl-L-norvalylamino-2-carboxyethyl)phosphinic acid
27. (1-Aminoethyl)(2-sarcosyl-L-alanyl-L-norvalylamino-2-carboxyethyl)phosphinic acid
28. (1-Aminoethyl)(2-L-alanyl-S-benzyl-L-cysteylamino-2-carboxyethyl)phosphinic acid
29. (1-Aminoethyl)(2-L-norvalyl-S-benzyl-L-cysteylamino-2-carboxyethyl)phosphonic acid
30. (1-Aminoethyl)(2-N-acetyl-L-norvalylamino-2-carboxyethyl)phosphinic acid
31. (1-Aminoethyl)[2-(N-L-noevalyl-N-methylamino)-2-carboxyethyl]phosphonic acid
32. (1-Aminoethyl)[2-(2-aminobutyroylamino)-2-carboxyethyl]phosphonic acid
33. (1-Aminoethyl)[2-(2-amino-4-methoxybutyroylamino)-2-carboxyethyl]phosphinic acid
34. (1-Aminoethyl)(2-L-prolylamino-2-carboxyethyl)phosphinic acid
35. (1-L-Norbalylaminoethyl)(2-L-norvalylamino-2-carboxyethyl)phosphinic acid
36. (1-L-Alanylaminoethyl)(2-L-norvalylamino-2-carboxyethyl)phosphinic acid
37. (1-Aminoethyl)(2-L-norvalyl-L-methionylamino-2-carboxyethyl)phosphinic acid
38. (1-Aminoethyl)(2-L-norvalyl-S-methyl-L-cysteinylamino-2-carboxyethyl)phosphinic acid
39, (1-Aminoethyl)(2-L-norvalyl-S-benzyl-L-crystinylamino-2-carboxyethyl)phosphinic acid
40. (1-Aminoethyl)(2-L-alanyl-L-alanyl-2-carboxyethylphosphinic acid Representative methods for the production of the compounds of our invention will now be described. These are examples and do not define the limits of procedures for the preparation of the compounds of our invention.

Typical methods of formation of the compounds of our invention are procedures A, B and C, shown below.

Procedure A

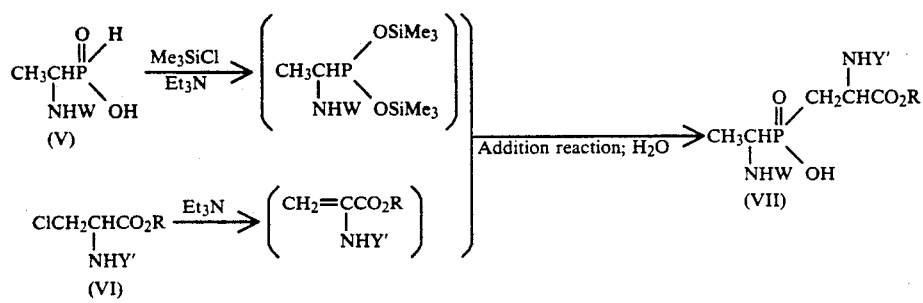

In the above, W is a protective group for amino; Y' is amino acid residue or oligopeptide residue with protection; and R is alkyl.

It is a method in which phosphine represented by (V) is allowed to react with trimethylsilyl chloride in the presence of triethylamine to form an intermediate silyl ester while chloroalanine derivative (VI) forms dehydroalanine by the action of triethylamine. After the addition reaction the system is brought into contact with water to form the desired aminoethylphosphinic acid derivative represented by (VII).

This reaction may be carried out by any known procedure, such as that using the Michael addition of phosphonous acid to acrylic ester (Tetrahedrom Letters 25, 4741, 1984).

Procedure B

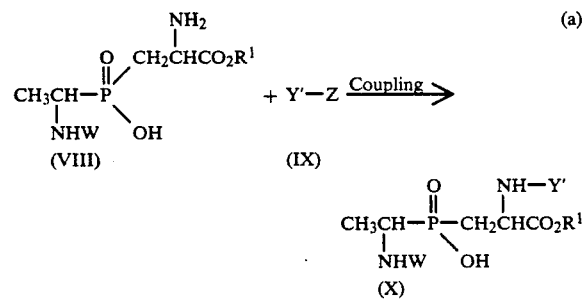

In the above, W and Y' are as defined earlier, and $R^1$ has the same meaning as $R^1$ in Formula (I). Z is the active site of carboxyl in hydroxysuccinimide ester, etc.

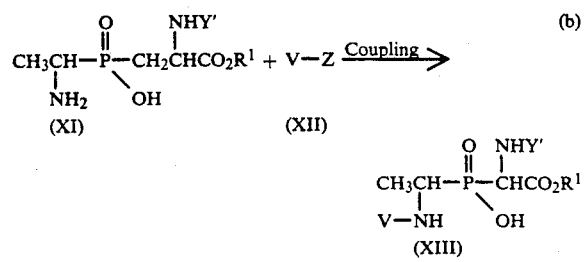

In the above, Y' and Z are as defined earlier and $R^1$ is as in Formula (I). V is protected amino acid or oligopeptide residue.

The method is one in which amino compounds represented by (VIII) and (XI) and active derivatives of protected amino acid or protected oligopeptide represented by (IX) and (XII) enter a coupling reaction to form aminoethylphosphinic acid derivatives coupled with amino acid or oligopeptide, represented by (X) and (XIII).

Coupling may be carried out using reactions commonly used in peptide synthesis. To give a typical example: amino compounds represented by (VIII) and (XI) and hydroxysuccinimide ester of protected amino acid or oligopeptide represented by (IX) and (XII) are allowed to react at room temperature using inert solvent such as tetrahydro furan, dioxane, chloroform or acetonitrile in the presence of a base such as triethylamine to obtain the intended products (X) and (XIII) which are coupled with amino acid or oligopeptide.

Procedure C (deblocking)

The aminoethylphosphinic acid derivatives of our invention are obtained by removing the protective groups of compounds obtained by Procedure A or Procedure B. Deprotection or deblocking may be carried out conventionally. The usual method employed in peptide synthesis and phosphinic acid synthesis and suitable for deblocking of the specific protective groups should be used. The reaction is conducted by catalytic reduction using hydrogen metal catalyst or deblocking agents such as HBr-acetic acid, trifluoroacetic acid, concentrated hydrochloric acid, dilute HCl-acetic acid, formic acid, alkali hydroxide and sodium-liquid ammonia.

When the desired compound is a mineral acid or organic hydrochloride of amine, the agent may be introduced into the inner salt. A typical example in these instances is to treat the compound with propylene oxide.

There is no special requirement regarding the methods of separation and purification in Procedures A and C. The familiar methods such as solvent extraction, washing, crystallization, use of ion exchange resin or normal or reverse phase chromatography.

The aminoethylphosphinic acid derivatives of our invention exhibit outstanding antibacterial activity against Gram positive organisms such as *Staphylococcus aureus* and *Streptococcus faecalis* and Gram negative organisms such as *E. coli, Klebsiella pneumoniae, Proteus vulgaris, Salmonella typhimurium* and *Serratia marcescens*.

These compounds are therefore useful in the therapy of various infectious diseases. These include pneumonia, bronchitis, laryngitis, pharyngitis, conjunctivitis, bactrial endocarditis, gonorrhea, intrauterine infection, urethritis, cystitis, pyelitis, infection following burns, postoperative wound infection and infectious stomatitis.

The compounds of our invention may be used by themselves, although a diluent is ordinarily used.

Diluents which may be used with the compounds of our invention may be solid, semi solid or liquid. Examples include molding agent, extender, binder, wetting agent, disintegrator, surfactant, lubricant, dispersant, buffer, flavor and odor corrigents, dye, perfume, preservative, solution helper, solvent coater, sugar coater and capsules. Two or more of these diluents may be used together. Specific examples are water, gelatin, sugars such as lactose and glucose, starches such as corn, wheat, rice and arrowroot starches, fatty acids such as stearic acid, fatty acid salts such as calcium stearate and magnesium stearate, talc, plant oils, alcohols such as stearyl and benzyl alcohols and polyalkylene glycol, gum, petroleum, mineral oil, physiological saline, and dextrose or similar sugars.

The drug of our invention may be prepared by conventional method. For instance, the compound may be mixed with diluent and granulated, and this preparation may be mixed with diluent and made into tablets or packaged in the form of granules. Capsules, pellets and powder should contain 5–100, preferably 25–100, wt % compound.

When the preparation is to be a liquid for oral administration, a suspension or syrup containing 0.5–10 wt % compound should be made.

Preparations for oral administration should be sterile and, when required, isotonic with blood.

Suitable solvents for injection are sterile water, lidocaine hydrochloride (for intramuscular injection), physiological saline, glucose, intravenous injection fluid and electrolyte solution (for intravenous and instillation purposes). The injection fluid should contain 0.5–20, preferably 1–10 wt % compound.

The dose is determined by the physician in accordance with the species (man or animal) to be treated, age, sex, body weight, differential sensitivity, route of administration, time of administration, state of the illness, condition of the body, character of the drug, formulation, type and effective ingredient.

To find the effective dose using animals, the effective ingredient should be given at 0.1–500, preferably 1–100, mg/kg body weight when orally administered; when the route is other than oral, the level of the effective ingredient should be 0.01–200, preferably 0.05–50 mg.

In selecting the dose for man, the following ranges (based on sensitivity differential and safety as determined in animals) are permitted: for oral administration, 0.–250, preferably 0.5–50 mg/kg/day, and for non oral routes, 0.01–100, preferably 0.05–50 mg/kg/day.

Depending on conditions, satisfactory results may be obtained with less than the above minimal doses, or there may be instances when more than the above maximum doses may be required. When large doses are given, each daily dose should be divided into several smaller doses.

The compounds of our invention exhibit high antibacterial activity over a wide range, and should be useful in the therapy of various types of infectious diseases.

The invention is explained in detail by means of the examples which follow. It should not be construed that the invention is limited to these examples.

The invention is explained in detail by means of the examples which follow. It should not be construed that the invention is limited to these examples.

EXAMPLE 1

(Procedure A + Procedure B)

(a) Synthesis of N-carbobenzoxydehydroalanine p-nitrobenzyl ester

To 20 ml solution of 2.18 g (5 mmols) N-carbobenzoxy-$\beta$-bromoalanine p-nitrobenzyl ester in tetrahydrofuran, 1.01 g (10 mmols) triethylamine was added and the mixture was stirred at room temperature for 30 minutes. Solvent was removed under reduced pressure, water was added and the crystals which formed were filtered to obtain 1.80 g (yield 100%) of the desired compound.

IR (KBr, cm$^{-1}$) 1710, 1520, 1310

NMR (CDCl$_3$, $\delta$) 5.15 (2H, s, —CH$_2$O), 5.33 (2H, s, —CH$_2$O), 5.85, 6.30 (2H, m, CH$_2$=C), 7.25 (/H, m, NHCO), 7.35 (5H, s, Ph), 7.50, 8.22 (4H, ABq,

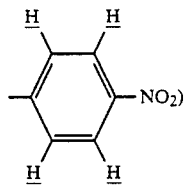

(b) Synthesis of (1-carbobenzoxyaminoethyl)(2-carbobenzoxyamino-2-p-nitrobenzyl-oxycarbonyoethyl)-phosphinic acid To 25 ml of solution of 729 mg (3 mmols) 1-carbobenzoxyaminoethylphosphinic acid in methylene chloride, 0.93 ml (6.6 mmols) triethylamine and 0.84 ml (6.6 mmols) trimethylsilyl chloride were added followed by 1.21 g (3.4 mmols) N-carbobenzoxy-dehydroalanine-p-nitrobenzyl ester obtained in (a). The mixture was stirred at room temperature for 2 days. The reaction fluid was washed with water and saturated physiological saline and dried, solvent was removed, and the residue was purified by silicagel chromatography (solvent: methylene chloride containing 15% methanol) to obtain 1.32 g (yield 73%) of the desired compound.

IR (KBr, cm$^{-1}$) 1710, 1530, 1350

NMR (CDCl$_3$, $\delta$) 1.23 (3H, m, CH$_3$—), 2.35 (2H, m, PCH$_2$—), 3.95 (1H, m, —CH), 5.1 (7H, m, —CH$_2$—X3, —CH—), 5.55 (/H, m, CONH), 7.20 (10H, s, —Ph×2), 7.30 8.00 (4H, ABq,

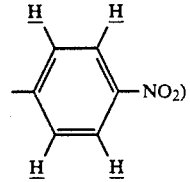

(c) Synthesis of (1-aminoethyl)(2-amino-2-carboxyethyl)phosphinic acid

To a solution of 380 mg (0.63 mmol) (1-carbobenzoxyaminoethyl)(2-carbobenzoxyamino-2-p-nitrobenzyloxycarbonylethyl)phosphinic acid obtained in (b) in 15 ml methanol, palladium black was added and the mixture was stirred for 3 hours in a stream of hydrogen. Catalyst was filtered, methanol was removed under reduced pressure, the residue was treated with water and washed with ether, liquid was removed under reduced pressure, 2 ml HBr-saturated acetic acid was added to the oily material, and the preparation was stirred at room temperature for 30 minutes. To the reaction fluid, 15 ml ether was added, and the resulting crystals were filtered and washed with ether. The crystals were then dissolved in 1 ml methanol, 5 ml propylene oxide was added, and the mixture was allowed to stand. The crystals which formed were filtered and washed with ether to obtain 67 mg (yield 54%) of the desired compound. The physical properties of this compound are shown in Table 1 under compound No. 1.

EXAMPLE 2

(Procedure A+Procedure C+Procedure B)

(a) (1-Carbobenzoxyaminoethyl)(2-tert-butyloxycarbonylamino-2-methoxycarbonylethyl)phosphinic acid A solution of 2.24 g (9.43 mmols) N tertbutyloxycarbonyl- -chloroalanine methyl ester was prepared in 15 ml tetrahydrofuran and 1.05 g (1.44 mmols) triethylamine was added. The mixture was stirred for 3 hours at room temperature. The resulting triethylamine hydrochloride was filtered, the material was washed with tetrahydrofuran, and solvent was removed under reduced pressure, to obtain N-tert-butyl-oxycarbonyl-dehydroalanine methyl ester. Meanwhile 3.44 g (14.1 mmols) N-carbobenzoxy-1-aminoethylphosphinic acid was dissolved in 40 ml acetonitrile. After cooling the solution to 0° C., 3.29 g (4.53 mmols) triethylamine was added, after which 3.53 g (4.12 mmols) trimethylsilane chloride was added slowly. After stirring the mixture for 30 minutes at room temperature, 15 ml solution of N tertbutyloxycarbonyl-dehydroalanine methyl ester in acetonitrile was added and the mixture was stirred for 6 hours at 85° C. After cooling, the solvent was removed under reduced pressure, and the residue was dissolved in ethyl acetate and washed with dilute hydrochloric acid and saturated sodium chloride solution. It was then dried with magnesium sulfate, solvent was removed, and the product was purified by silicagel column chromatography (solvent =chloroform methanol) to obtain 3.45 g of the desired substance. The yield was 82%.

IR (KBr, cm$^{-1}$) 1750, 1720, 1700, 1535

NMR (CDCl$_3$δ) 1.36 (dd, J=7Hz, 14Hz, 3H, CH$_3$), 1.42 (s, 9H, C(CH$_3$)$_3$),
2.12–2.60 (m, 2H, PCH$_2$), 3.70 (s, 3H, OCH$_3$), 3.80–4.87 (m, 2H, CH×2), 5.12 (s, 2H, CH$_2$Ph), 5.28–5.78 (m, 2H, CONH×2), 7.32 (s, 5H, Ph)

(b) (1-Carbobenzoxyaminoethyl)(2-amino-2-methoxycarbonylethyl)phosphinic acid hydrochloride A solution of 1.70 g (3.82 mmols) of (1-carbobenzoxyaminoethyl)(2-tert-butyl-oxycarbonylamino-2-methoxycarbonylethyl)phosphonic acid obtained in (a) in 20 ml formic acid was stirred for 6 hours at room temperature, after which the solvent was removed under reduced pressure. The residue was dissolved in dilute hydrochloric acid and washed with ethyl acetate. After removing the solvent under reduced pressure, the product was dried to obtain 1.299 g of the desired compound. The yield was 89%.

NMR (CD$_3$OD, δ) 1.33 (dd, J=7Hz, 14Hz, 3H, CH$_3$), 2.03–2.60 (m, 2H, PCH$_2$), 3.73 (s, 3H, OCH$_3$), 3.57–4.50 (m, 2H, CH×2), 5.01 (s, 2H, CH$_2$Ph), 7.28 (s, 5H, Ph)

(c) (1-Carbobenzoxyaminoethyl)(2-N-carbobenzoxy-L-phenylalanylamino-2-methoxy-carbonylethyl)phosphinic acid In a mixture of 30 ml tetrahydrofuran and 10 ml acetonitrile, 620 mg (1.63 mmols) (1-carbobenzoxyaminoethyl)(2-amino-2-methoxycarbonylethyl)phosphinic acid hydrochloride and 710 mg (1.79 mmols) N-carbobenzoxy-L-phenylalanine hydroxysuccinimide ester were dissolved, and 330 mg (3.26 mmols) triethylamine was added. The mixture was stirred for 4 hours at room temperature. Solvent was removed under reduced pressure, and the residue was dissolved in dilute hydrochloric acid and extracted with ethyl acetate. The extract was washed with saturated sodium chloride solution and dried with magnesium sulfate. Solvent was removed under reduced pressure and the product was purified by silicagel column chromatography (solvent =chloroform containing 10% methanol) to obtain 740 mg of the desired product. The yield was 73%.

IR (KBr, cm$^{-1}$) 1750, 1715, 1675, 1535

NMR (CDCl$_3$, δ) 1.27 (dd, J=7Hz, 14Hz, 3H, CH$_3$), 2.02–2.57 (m, 2H, PCH$_2$), 2.78–3.17 (m, 2H, CH$_2$), 3.68 (s, 3H, OCH$_3$), 3.70–4.77 (m, 3H, CH×3), 5.10 (s, 2H, CH$_2$Ph), 5.15 (s, 4H, CH$_2$Ph×2), 5.40 –6.53 (m, 3H, CONH×3), 7.27 (s, 5H, Ph), 7.32 (s, 5H, Ph), 7.40 (s, 5H, Ph)

(d) (1-Aminoethyl)(2-L -phenylalanylamino-2-carboxyethyl)phosphinic acid

To a solution of 540 mg (0.88 mmol)(1-carbobenzoxyaminoethyl)(2-N-carbobenzoxy-L-phenylalanylamino-2-methoxycarbonylethyl)phosphonic acid in 8 ml methanol, 0.88 ml 2N KOH was added and the mixture was stirred at room temperature for 20 hours. Solvent was removed under reduced pressure and the residue was dissolved in dilute hydrochloric acid and extracted with ethyl acetate. The extract was washed with saturated sodium chloride solution and dried with magnesium sulfate, after which solvent was removed under reduced pressure to obtain 470 mg (1-carbobenzoxyaminoethyl)(2-N-carbobenzoxy-L-phenylalanylamino- 2-carboxyethyl)phosphinic acid was obtained. This was dissolved in 12 ml methanol, 3 ml acetic acid and 2 ml water, 150 mg palladium black was added, and hydrogen was forced in for 1 hour at room temperature. Catalyst was filtered, the material was washed with water, solvent was removed under reduced pressure, and the product was purified by reverse phase column chromatography (RP-8; solvent-=water) to obtain 210 mg of the desired compound. The yield was 80%.

The physical properties of this compound are shown in Table 1 under Compound No. 4.

EXAMPLE 3

(Procedure C)

(1-Aminoethyl)(2-L-phenylalanylamino-2-methoxycarbonylethyl)phosphinic acid

A solution of 450 mg (0.74 mol) (1-carbobenzoxyaminoethyl) (2-N-carbobenzoxy-L-phenylalanylamino -2-methoxycarbonylethyl)phosphinic acid in a mixture of 8 ml methanol, 2 ml acetic acid and 1 ml water was prepared and 150 mg palladium black was added. After forcing in hydrogen at room temperature for 1 hour, catalyst was filtered and the material was washed with water. The filtrate was concentrated and purified by reverse phase column chromatography (RP-8; solvent=water) to obtain 190 g of the desired material. The yield was 72%. The physical properties of this substance are shown in Table 1 under Compound No. 5.

EXAMPLE 4-1

(Procedure B+Procedure C)

(a) (1-Carbobenzoxyaminoethyl)(2-N-carbobenzoxy-L-norvalylamino-2-methoxycarbonylethyl)phosphinic acid A solution of 480 mg (1.26 mmols) (1-carbobenzoxyaminoethyl) (2-amino 2-methoxycarbonylethyl)phosphinic acid hydrochloride and 480 mg (1.39 mmols) N-carbobenzoxy L norvaline hydroxysuccinimide ester in 25 ml tetrahydrofuran was prepared, and 270 mg (2.65 mmols) triethylamine was added. The mixture was stirred at room temperature for 7 hours. Dilute hydrochloric acid was added and the material was extracted with ethyl acetate. The extract was washed with saturated sodium chloride solution and dried with magnesium sulfate. Solvent was removed under reduced pressure and the product was purified by silicagel column chromatography (solvent=chloroform-methanol) to obtain 380 mg of the desired material. The yield was 52%.

NMR (CDCl$_3$, $\delta$) 0.87-2.47 (m, 12H, CH$_2$CH$_2$CH$_3$, CH$_3$, PCH$_2$), 3.70 (s, 3H, OCH$_3$), 3.30-4.40 (m, 3H, CH$\times$3), 5.16 (s, 4H, CH$_2$Ph$\times$2), 4.63-5.53 (m, 2H, CONH$\times$2), 5.60-6.50 (m, /H, CONH), 7.27 (s, 10H, Ph$\times$2)

(b) (1-Aminoethyl)(2-L-norvalylamino-2-carboxyethyl)-phosphinic acid

A solution of 380 mg (0.67 mmols) (1-carbobenzoxyaminoethyl) (2-N-carbobenzoxy-L-norvalylamino-2-methoxycarbonylethyl)phosphinic acid was prepared in 15 ml methanol, and 0.67 ml 2N KOH was added. The mixture was stirred at room temperature for 1 hour and at 60° C. for 1 hour. After cooling, solvent was removed under reduced pressure and the residue was dissolved in water and washed with ethyl acetate. The tract was washed with saturated sodium chloride solution and dried with magnesium sulfate. Solvent was removed to obtain 340 mg (1-carbobenzoxyaminoethyl) (2-N-carbobenzoxy-L-norvalylamino-2-carboxyethyl)phosphinic acid. This was dissolved in a mixture of 8 ml methanol, 2 ml acetic acid and 1 ml water, 120 mg palladium black was added, and hydrogen was forced in for 1 hour at room temperature. Catalyst was filtered off, the material was washed with water, solvent was removed, and the product was purified by reverse phase column chromatography (RP-8, solvent=water) to obtain 110 mg of the desired substance. The yield was 62%. The physical properties of this compound are shown in Table 1 under No. 6-1.

EXAMPLE 4-2

In place of N-carbobenzoxy-DL-1-aminoethylphosphinic acid described in Example 4-1, a), optically active N-carbobenzoxy-D-1-aminoethylphosphinic acid was used. Otherwise the procedure was identical with that of Example 4-1. The two diastereomers obtained by this procedure were separated by TLC to obtain (D-1-aminoethyl)(2-L-nor-valylamino -2-L- or -D-carboxyethyl)phosphinic acid (Compound No. 6 2).

Following the procedures described for Example 1 through Example 4-1, aminoethylphosphinic acid derivatives (Compounds 7-31) shown in Table 1 were synthesized. Their physical properties are shown in Table 1.

TABLE 1

Compound No. 1

(1-Aminoethyl)(2-amino-2-carboxyethyl)phosphinic acid
mp 270° C. (decomp.)
IR (KBr, cm$^{-1}$) 1640
NMR (D$_2$O, $\delta$) 1.50 (3H, m, CH$_3$), 2.30 (2H, m, PCH$_2$—)

Compound No. 2

(Aminoethyl)[2-(3-phenylpropionylamino)-2-carboxyethyl]phosphinic acid
mp 157°-58° C. (decomp.)
IR (KBr, cm$^{-1}$) 1710, 1633, 1570, 1530
NMR (D$_2$O+NaOD, $\delta$) 1.23 (3H, dd, J=7Hz, 14Hz, —CH$_3$), 1.66-2.23 (2H, m, —CH$_2$—), 2.33-3.10 (4H, m, —CH$_2$CH$_2$—), 3.95-4.60 (2H, m, —CH$\times$2), 7.20 (5H, s, Ph)

Compound No. 3

(1-Aminoethyl)[2-(3-phenylpropionylamino)-2-methoxycarbonylethyl]phosphinic acid
mp 98°-120° C.
IR (KBr, cm$^{-1}$) 1745, 1650, 1545
NMR (D$_2$O, $\delta$) 1.32 (3H, dd, J=7Hz, 14Hz, CH$_3$), 1.83-2.36 (2H, m, —CH$_2$), 2.40-3.43 (4H, m, —CH$_2$CH$_2$—) 3.66 (3H, s, OCH$_3$), 4.16-4.80 (2H, m, —CH—$\times$2), 7.23 (5H, s, Ph)

Compound No. 4

(1-Aminoethyl)(2-L-phenylalanylamino 2-carboxyethyl)-phosphinic acid
mp 95.5°-99° C.
IR (KBr, cm$^{-1}$) 1680-1520
NMR (D$_2$O+NaOD, $\delta$) 1.28 (dd, J=7Hz, 14Hz, 3H, CH$_3$), 1.73-2.30 (m, 2H, PCH$_2$), 2.73-3.13 (m, 2H, CH$_2$Ph), 3.50-4.51 (m, 3H, —CH—$\times$3), 7.38 (s, 5H, Ph)

Compound No. 5

(1-Aminoethyl)(2-L-phenylalanylamino-2-methoxycarbonyl-ethyl)-phosphinic acid
mp 95.5°-99° C.
IR (KBr, cm$^{-1}$) 1750, 1680, 1540
NMR (D$_2$O+D$_2$SO$_4$, $\delta$) 1.47 (dd, J=7Hz, 14Hz, 3H, CH$_3$), 2.10-2.67 (m, 2H, PCH$_2$), 3.23 (d, J=7Hz, 2H, CH$_2$Ph), 3.40-3.97 (m, /H, CH), 3.73 (s, 1.5H, OCH$_3$), 3.77 (s, 1.5 H, OCH$_3$), 4.30 (t, J=7Hz, /H, CH), 4.40-5.03 (m, /H, CH), 7.33 (s, 5H, Ph)

Compound No. 6-1

(1-Aminoethyl)(2-L-norvalylamino- 2-carboxyethyl)-phosphinic acid
mp 236°-241° C. (decomp.)
IR (KBr, cm$^{-1}$) 1680-1520
NMR (D$_2$O, $\delta$) 0.96 (t, J=6Hz, 3H, CH$_3$), 1.43 (dd, J=7Hz, 14Hz, 3H, CH$_3$), 1.15-2.50 (m, 6H, —CH$_2$CH$_2$—, PCH$_2$), 3.10-4.50 (m, 3H, CH$\times$3) Compound No. 7

(1-Aminoethyl)(2-D-norvalylamino-2-carboxyethyl)-phosphonic acid
mp 197°-218° C. (decomp.)
IR (KBr, cm$^{-1}$) 1690-1510
NMR (D$_2$O, $\delta$) 0.97 (t, J=6Hz, 3H, CH$_3$), 1.45 (dd, J=7Hz, 14Hz, 3H, CH$_3$), 1.50-2.53 (m, 6E, —CH$_2$CH$_2$—, PCH$_2$), 3.15-4.60 (m, 3H, CH$\times$3)

Compound No. 8

(1-Aminoethyl)(2-L-leucylamino-2-carboxyethyl)-phosphinic acid
mp 170°–180° C. (decomp.)
IR (KBr, cm$^{-1}$) 1690–1520
NMR (D$_2$O, δ) 0.96 (d, J=5.0Hz, 6H, CH$_3$×2), 1.37 (dd, J=14.0, 7.0Hz, 3H, CH$_3$), 1.50–2.45 (m, 5H, CH$_2$CH$_3$ 3.10–4.55 (m, 3H, CH×3)

Compound No. 9

(1-Aminoethyl)(2-L-isoleucylamino-2-carboxyethyl)-phosphonic acid
mp 175°–195° C. (decomp.)
IR (KBr, cm$^{-1}$) 1690–1510
NMR (D$_2$O, δ) 0.68–1.16 (m, 6H, CH$_3$×2), 1.42 (dd, J=14.0, 7.0Hz, 3H, CH$_3$0, 1.50–2.55 (m, 5H, CHCH$_2$, PCH$_2$), 3.10–4.45 (m, 3H, CH×3)

Compound No. 10

(1-Aminoethyl)(2-L-methionylamino-2-carboxyethyl)phosphonic acid
mp 194°–205° C. (decomp.)
IR (KBr, cm$^{-1}$) 1690–1510
NMR (D$_2$O, δ) 1.43 (dd, J=14.0, 7.0Hz, 3H, CH$_3$), 2.13 (s, 3H, SCH$_3$), 1.70–2.85 (m, 6H, CH$_2$CH$_2$, PCH$_2$), 3.10–4.50 (m, 3H, CH×3)

Compound No. 11

(1-Aminoethyl)[2-S-(1-methyltetrazol 5-yl)cysteylamino-2-carboxyethyl]phosphonic acid
mp 152°–155° C. (decomp.)
IR (KBr, cm$^{-1}$) 1680–1520
NMR (D$_2$O, δ) 1.20 (dd, J=7Hz, 14Hz, 3H, CH$_3$), 1.90–2.55 (m, 2H, PCH$_2$), 3.00–4.27 (m, 5H, SCH$_2$CH, CH×2), 3.80 (s, 3H, NCH$_3$)

Compound No. 12

(1-Aminoethyl)(2-L-alanylamino-2-carboxyethyl)-phosphinic acid
mp 162°–167° C. (decomp.)
IR (KBr, cm$^{-1}$) 1690–1520
NMR (D$_2$O, δ) 1.45 (dd, J=7Hz, 14Hz, 3H, CH$_3$), 1.57 (d, J=7Hz, 3H, CH$_3$), 2.03–2.47 (m, 2H, PCH$_2$), 3.05–3.55 (m, /H, CH), 3.90–4.55 (m, 2H, CH×2)

Compound No. 13

(1-Aminoethyl)(2-L-lysylamino-2-carboxyethyl)-phosphinic acid
mp 105°–139° C.
IR (KBr, cm$^{-1}$) 1680–1500
NMR (D$_2$O, δ) 1.45 (dd, J=13.6, 7.3Hz, 3H, CH$_3$), 1.45–1.60 (m, 2H, CH$_2$), 1.65–1.85 (m, 2H, CH$_2$), 1.88–2.55 (m, 4H, PCH$_2$, CH$_2$), 3.06 (t, J=7.2Hz, 2H, CH$_2$), 3.25–3.45 (m, /H, CH), 3.98 (t, J=6.3 Hz, /H, CH), 4.6–4.55 (m, /H, CH)

Compound No. 14

(1-Aminoethyl)(2-L-serylamino-2-carboxyethyl)-phosphinic acid
mp 158°–159° C.
IR (KBr, cm$^{-1}$) 1690–1510
NMR (D$_2$O, δ) 1.42 (dd, J=13.6, 7.3Hz, 3H, CH$_3$), 1.90–2.43 (m, 2H, PCH$_2$), 3.25–3.45 (m, /H, CH), 3.75–4.25 (m, 3H, CHCH$_2$O), 4.45–4.70 (m, /H, CH)

Compound No. 15

(1-Aminoethyl)(2-o-benzyl-L-serylamino-2-carboxyethyl)-phosphonic acid
mp 173°–184° C. (decomp.)
IR (KBr, cm$^{-1}$) 1780, 1640–1570, 1530
NMR (D$_2$O, δ) 1.32–1.53 (m, 3H,, CH$_3$), 1.83–2.40 (m, 2H, PCH$_2$), 3.25–3.47 (m, /H, CH), 3.82–4.05 (m, 2H, CH$_2$O), 4.27–4.35 (m, /H, CH), 4.35–4.52 (m, /H, CH), 4.65 (s, 2H, OCH$_2$Ph), 7.44 (s, 5H, Ph)

Compound No. 16

(1-Aminoethyl)(2-S-benzyl-L-cysteylamino-2-carboxyethyl)-phosphonic acid
mp 189°–200° C. (decomp.)
IR (KBr, cm$^{-1}$) 1690–1495
NMR (D$_2$O, δ) 1.35–1.53 (m, 3H, CH$_3$), 1.88–2.43 (m, 2H, PCH$_2$), 2.83–3.20 (m, 2H, CH$_2$S), 3.25–3.43 (m, /H, CH), 3.88 (s, 2H, SCH$_2$Ph), 4.09 (t, J=6.5Hz, /H, CH), 4.35–4.50 (m, /H, CH), 7.44 (s, 5H, Ph)

Compound No. 17

(1-Aminoethyl)(2-S-methyl-L-cysteylamino-2-carboxyethyl)-phosphonic acid
mp 173°–179° C. (decomp.)
IR (KBr, cm$^{-1}$) 1690–1490
NMR (D$_2$O, δ) 1.23 (dd, J=14.0, 7.3Hz, 3H, CH$_3$), 1.98 (s, 3H, SCH$_3$), 1.83–2.25 (m, 2H, PCH$_2$), 2.70–3.05 (m, 2H, CH$_2$S), 3.10–3.25 (m, /H, CH), 4.00–4.10 (m, /H, CH), 4.30–4.65 (m, /H, CH)

Compound No. 18

(1-Novalylaminoethyl)(2-L-phenylalanylamino-2-arboxyethyl)-phosphinic acid
mp 200°–217° C.
IR (KBr, cm$^{-1}$) 1680–1530
NMR (D$_2$O, δ) 0.87–2.83 (m, 12H, CH$_2$CH$_2$CH$_3$, CH$_3$, PCH$_2$), 3.03–3.50 (m, 2H, CH$_2$Ph), 3.70–4.65 (m, 4H, CH×4), 7.34 (s, 5H, Ph)

Compound No. 19

(1-Acetoaminoethyl)(2-L-norvalylamino-2-carboxyethyl)-phosphonic acid
mp 163°–169° C. (decomp.)
IR (KBr, cm$^{-1}$) 1680, 1655, 1545
NMR (CDCl$_3$, δ) 0.95 (t, J=7.2Hz, 3H, CH$_3$), 1.05–1.53 (m, 5H, CH$_3$, CH$_2$), 1.75–2.30 (m, 4H, CH$_2$, PCH$_2$),
2.04 (s, 3H, COCH$_3$), 3.90–4.15 (m, 2H, CH×2), 4.40–4.80 (m, /H, CH)

Compound No. 20

(1-Aminoethyl)(2-L-alanyl-L-norvalylamino-2-carboxyethyl)-phosphonic acid
mp 190°–205° C. (decomp.)
IR (KBr, cm$^{-1}$) 1690–1520
NMR (D$_2$O, δ) 0.93 (t, J=7.0Hz, 3H, CH$_3$), 1.42 (dd, J=13.3, 7.3Hz, 3H, CH$_3$), 1.57 (d, J=7.1H, 3H, CH$_3$), 1.25–2.40 (m, 6H, CH$_2$CH$_2$, PCH$_2$), 3.20–3.40 (m, /H, CH), 4.12 (q, J=7.1Hz, /H, CH), 4.27–4.66 (m, 2H, CH×2)

Compound No. 21

(1-Aminoethyl)(2-L-phenylalanyl-L-norvalylamino-2-carboxyethyl)phosphonic acid
mp 219°–223° C. (decomp.)
IR (KBr, cm$^{-1}$) 1680, 1655, 1598, 1530

NMR (D₂O, δ) 0.68 (t, J=7.2Hz, 3H, CH₃), 1.95-2.20 (m, 9H, CH₂CH₂, CH₃, PCH₂), 2.85-3.20 (m, 3H, CH₂Ph, CH), 3.95-4.35 (m, 3H, CH×3), 7.03-7.15 (m, 5H, Ph)

Compound No. 22

(1-Aminoethyl)(2-L-norvalyl-1-L-norvalylamino-2-carboxyethyl)-phosphonic acid
mp 220°-226° C. (decomp.)
IR (KBr, cm⁻¹) 1680, 1655, 1595, 1530
NMR (D₂O, δ) 0.71 (t, J=7.4Hz, 3H, CH₃), 0.75 (t, J=7.4Hz, 3H, CH₃), 1.05-1.35 (m, 7H, CH₂×2, CH₃), 1.43-2.20 (m, 6H, CH₂×2, PCH₂), 3.00-3.20 (m, /H, CH), 3.82 (t, J=6.5Hz, /H, CH), 4.05-4.30 (m, 2H, CH×2)

Compound No. 23

(1-Aminoethyl)(2-L-leucyl-L-norvalylamino-2-carboxyethyl)-phosphinic acid
mp 216°-220° C. (decomp.)
IR (KBr, cm⁻¹) 1680, 1655, 1595, 1530
NMR (D₂O, δ) 0.65-0.85 (m, 9H, CH₃×3), 1.08-1.35 (m, 5H, CH₃, CH₂), 1.40-2.20 (m, 7H, CH₂, CH₂CH, PCH₂), 3.05-3.25 (m, /H, CH), 3.65 (t, J=6.7Hz, /H, CH), 4.05-4.28 (m, 2H, CH×2)

Compound No. 24

(1-Aminoethyl)(2-L-isoleucyl-L-norvalylamino-2-carboxyethyl)-phosphinic acid
mp 218°-221° C. (decomp.)
IR (KBr, cm⁻¹) 1695-1510
NMR (D₂O, δ) 0.65-0.90 (m, 9H, CH₃×3), 0.95-2.15 (m, 12H, CH₃, CH₂CH₂, CH₂CH, PCH₂), 3.05-3.25 (m, /H, CH), 3.68 (d, J=5.7Hz, /H, CH), 4.08-4.25 (m, 2H, CH×2)

Compound No. 25

(1-Aminoethyl)(2-sarcosyl-L-norvalylamino-2-carboxyethyl)-phosphinic acid
mp 201°-206° C.
IR (KBr, cm⁻¹) 1695-1520
NMR (D₂O, δ) 0.70 (t, J=7.4Hz, 3H, CH₃), 1.10-1.30 (m, 5H, CH₃, CH₂), 1.40-2.18 (m, 4H, CH₂, PCH₂), 2.57 (s, 3H, NCH₃), 3.03-3.20 (m, /H, CH), 3.74 (s, 2H, CH₂N), 4.05-4.30 (m, 2H, CH×2)

Compound No. 26

(1-Aminoethyl)(2-L-alanyl-L-alanyl-L-norvalylamino-2-carboxyethyl)phosphonic acid
mp 215°-224° C. (decomp.)
IR (KBr, cm⁻¹) 1690-1510
NMR (D₂O, δ) 0.72 (t, J=7.2Hz, 3H, CH₃), 1.05-2.20 (m, 15H, CH₃×3, CH₂CH₂, PCH₂), 3.05-3.23 (m, /H, CH), 3.91 (q, J=7.1Hz, /H, CH), 4.05-4.30 (m, 3H, CH×3)

Compound No. 27

(1-Aminoethyl)(2-sarcosyl-L-alanyl-L-norvalylamino-2-carboxyethyl)phosphinic acid
mp 205°-212° C. (decomp.)
IR (KBr, cm⁻¹) 1690-1520
NMR (D₂O, δ) 0.71 (t, J=7.3Hz, 3H, CH₃), 1.03-1.35 (m, 8H, CH₃×2, CH₂), 1.40-2.15 (m, 4H, CH₂, PCH₂), 2.57 (s, 3H, NCH₃), 3.08-3.22 (m, /H, CH), 3.73 (s, 2H, CH₂N), 4.10-4.30 (m, 3H, CH×3)

Compound No. 28

(1-Aminoethyl)(2-L-alanyl-S-benzyl-L-cysteylamino-2-carboxyethyl)phosphinic acid
MP 202°-209° C.
IR (KBr, cm⁻¹) 1685, 1655, 1595, 1530
NMR (D₂O, δ) 1.19 (dd, J=13.5, 7.3Hz, 3H, CH₃), 1.34 (d, J=6.8Hz, 3H, CH₃), 1.70-2.15 (m, 2H, PCH₂), 2.50-2.95 (m, 2H, CH₂S), 3.08-3.20 (m, /H, CH), 3.61 (s, 2H, SCH₂), 3.90-3.98 (m, /H, CH), 4.05-4.40 (m, 2H, CH×2), 7.19 (s, 5H, Ph)

Compound No. 29

(1-Aminoethyl)(2-L-norvalyl-S-benzyl-L-cysteylamino-2-carboxyethyl)phosphinic acid
mp 202°-209° C.
IR (KBr, cm⁻¹) 1670-1510
NMR (D₂O, δ) 0.71 (s, J=7.2Hz, 3H, CH₃), 1.05-2.20 (m, 9H, CH₃, CH₂CH₂, PCH₂), 2.53-2.98 (m, 2H, CH₂S), 3.02-3.20 (m, /H, CH), 3.63 (s, 2H, SCH₂), 3.65-3.95 (m, /H, CH), 4.08-4.40 (m, 2H, CH×2), 7.20 (s, 5H, Ph)

Compound No. 30

(1-Aminoethyl)(2-N-acetyl-L-norvalylamino-2-carboxyethyl)-phosphinic acid
mp 175°-190° C.
IR (KBr, cm⁻¹) 1710, 1655, 1630, 1535
NMR (D₂O, δ) 0.90 (t, J=7.2Hz, 3H, CH₃), 1.41 (dd, J=13.0, 7.2Hz, 3H, CH₃), 1.28-1.90 (m, 4H, CH₂CH₂), 2.04 (s, 3H, COCH₃), 1.92-2.40 (m, 2H, PCH₂), 3.25-3.40 (m, /H, CH), 4.23-4.38 (m, /H, CH)

Compound No. 31

(1-Aminoethyl)[2(N-L-norvalyl-N-methylamino)-2-carboxyethyl]phosphinic acid
mp 132°-146° C. (decomp.)
IR (KBr, cm⁻¹) 1680-1500
NMR (D₂O, δ) 0.96 (t, J=7.0Hz, 3H, CH₃), 1.12 (dd, J=14.0, 7.0Hz, 3H, CH₃), 1.45-2.53 (m, 6H, CH₂CH₂, PCH₂), 2.86, 3.08 (s, 3H, NCH₃), 3.10-4.53 (m, 3H, CH×3)

Test Examples

Antibacterial activity was tested by two methods.
Minimum inhibiting concentration (MIC, μg/ml) was determined by the method of Atherton et al (Antimicrobial Agent and Chemotherapy 15, 677, 1979). The results are shown in Table 2.
Of the 25 strains used in standard MIC determination, 16 were used to measure antibacterial activity according to the standard procedure of Japan Chemotherapy Society[1]

[1] Chemotherapy 16, 98, 1968; Ishiyama et. al.

Dilutions were doubled at each level beginning at 100 μg/ml. The growth medium was heart infusion broth (product of Eiken), Medium for the plating test had the composition shown in the following table. The results are shown in Table 3.

| Composition of medium (amount/liter, pH 7.0) | |
|---|---|
| L-Arginine | 0.1 gr |
| L-Aspartic cid | 0.1 |
| L-Cysteins | 0.1 |
| L-Glycine | 0.1 |
| L-Histidine | 0.1 |
| L-Phenylalanine | 0.1 |
| L-Proline | 0.1 |

-continued

| Composition of medium (amount/liter, pH 7.0) | |
|---|---|
| L-Serine | 0.1 |
| L-Threonine | 0.1 |
| L-Tryptophan | 0.1 |
| L-Tyrosine | 0.1 |
| L-valine | 0.1 |
| Guanine | 0.01 |
| Uracil | 0.01 |
| Cytosine | 0.01 |
| Adenine | 0.01 |
| D-Glucose | 5.0 |
| Yeast extract | 0.1 |
| Sodium citrate | 0.5 |
| KH$_2$PO$_4$ | 2.0 |
| KH$_2$PO$_4$ | 7.0 |
| MgSO$_4$.7H$_2$O | 0.1 |
| (NH$_4$)$_2$SO$_4$ | 1.0 |
| Agar | 15.0 |

TABLE 2

| | Antibacterial activity: MIC (μg/ml) [by Method 1] | | | |
|---|---|---|---|---|
| Organism | Compound No. 6-1 | Compound No. 10 | Compound No. 20 | Compound No. 6-2 |
| Staphylococcus aureus | 32 | 4 | 256 | 8 |
| Streptococcus faecalis | 16 | 2 | ≦0.25 | 1 |
| E. coli TEM 2 | 256 | 256 | ≦0.25 | 64 |
| E. coli DC 2 | 16 | 32 | ≦0.25 | 4 |
| E. coli | 16 | 64 | 0.5 | 8 |
| Salmonella typhimurium | 128 | >256 | 0.5 | 32 |
| Enterococcus cloacae | 64 | 256 | 0.5 | 16 |
| Klebsiella pneumoniae | — | >256 | ≦0.25 | 64 |
| Proteus vulgaris | 1 | 8 | 0.5 | 1 |
| Pseudomonas aeruginosa | >256 | >256 | 256 | >256 |
| Serratia marcescens | >256 | >256 | 0.5 | 128 |

What is claimed is:

TABLE 3

| | Antibacterial activity (MIC) [by Method 2] | | | | | | | |
|---|---|---|---|---|---|---|---|---|
| | Compound No. | | | | | | | |
| Organism | 20 | 21 | 22 | 23 | 24 | 25 | 26 | 27 |
| Staphylococcus aureus FDA 209 PCJ-1 | 0.78 | 6.25 | 0.39 | 0.39 | 0.19> | 3.1 | 0.09> | 0.19> |
| E. coli NIHJ JC-2 | 3.1 | 12.5 | 0.39 | 1.56 | 1.56 | 12.5 | >100 | >100 |
| E. coli K-12 C-600 | 0.19 | 0.39 | 0.09> | 0.19> | 0.19> | 0.39 | 0.19 | 1.56 |
| Klebsiella pneumoniae PCI-602 | >100 | 100 | 50 | 100 | >100 | >100 | >100 | >100 |
| Salmonella typhimurium IID-971 | 0.78 | 3.12 | 0.39 | 0.39 | 0.39 | 1.56 | >100 | >100 |
| Salmonella Schottmulleri 8006 | 0.19> | 0.09 | 0.09> | 0.19> | 0.19> | 0.19> | 0.78 | >1.56 |
| Salmonella enteriditis G-14 | 0.39 | 1.56 | 0.19 | 0.39 | 0.39 | 1.56 | >100 | >100 |
| Serratia marcescens IAM 1184 | 0.39 | 3.12 | 0.19 | 0.39 | 0.78 | 3.12 | 100 | 50 |
| Bacillus subtilis ATCC-6633 | 6.25 | 0.39 | 3.12 | 0.78 | 0.78 | 100 | 25 | >100 |
| Pseudomonas aeruginosa IFO-3445 | >100 | >100 | >100 | >100 | >100 | >100 | >100 | >100 |
| Proteus morgani IFO-3848 | 0.78 | 50 | 3.12 | 1.56 | 3.12 | 100 | 50 | >100 |
| Proteus vulgaris OK-19 | 1.56 | 12.5 | 0.39 | 0.78 | 0.39 | 6.25 | 12.5 | 6.25 |
| Proteus vulgaris HK-19 | 1.56 | 6.25 | 0.78 | 0.78 | 0.78 | 100 | 100 | >100 |
| Enterobacter aerogenes ATCC-13048 | 1.56 | 100 | 0.78 | 0.78 | 0.78 | 12.5 | >100 | >100 |
| Enterobacter cloacae 963 | 0.19> | 0.19 | 0.09> | 0.19> | 0.19> | 0.19> | >100 | >100 |
| Micrococcus luteus ATCC-9341 | 0.19> | 0.19> | 0.09> | 0.19> | 0.19> | 1.56 | 0.09 | 0.78 |

1. A compound represented by Formula I,

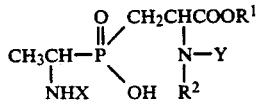

in which
X is hydrogen, acyl or amino acid
Y is hydrogen,
   unsubstituted or substituted alkylacyl wherein said alkyl substitutent is selected from the group consisting of amino, alkoxy and hydroxy; amino acid and $R^1$ and $R^2$ is hydrogen or alkyl.

2. The compound according to claim 1 in which the structure is represented by Formula III,

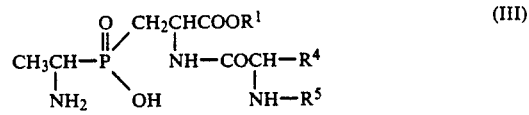

in which $R^1$ is hydrogen or alkyl, $R^4$ is alkyl or benzylthioalkyl, and $R^5$ is amino acid.

3. The compound according to claim 2, in which $R^1$ in Formula III is hydrogen, $R^4$ is n-propyl or benzylthiomethyl, and $R^5$ is alanyl, phenylalanyl, leucyl, isoleucyl, norvalyl, sarcosyl, sarcosylalanyl or alanylalanyl.

4. A compound represented by Formula I:

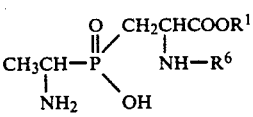

in which
$R^1$ is hydrogen or alkyl, and
$R^6$ is an amino acid residue with or without protection.

5. The compound according to claim 4 in which $R^1$ is hydrogen and $R^6$ is lysyl, seryl, alanyl, norvalyl, o-benzylseryl, or S-benzylcysteine.

6. The compound according to claim 1 being:
(1-aminoethyl) (2-amino-2-carboxyethyl)phosphinic acid;

(1-aminoethyl) (2-L-norvalylamino-2-carboxyethyl) phosphinic acid;

(1-aminoethyl) (2-L-methionylamino-2-carboxyethyl) phosphinic acid;

(1-aminoethyl) (2-L-alanyl-L-norvalylamino-2-carboxyethyl)phosphinic acid; or (1-aminoethyl) (2-L-norvalyl-L-norvalylamino-2-carboxyethyl)phosphinic acid.

* * * * *